United States Patent
Abel (10) Patent No.: US 6,765,203 B1
(45) Date of Patent: Jul. 20, 2004

(54) PALLET ASSEMBLY FOR SUBSTRATE INSPECTION DEVICE AND SUBSTRATE INSPECTION DEVICE

(75) Inventor: Alan Abel, San Jose, CA (US)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/355,757

(22) Filed: Jan. 31, 2003

(51) Int. Cl.[7] ............................................. G01R 31/305
(52) U.S. Cl. ...................... 250/310; 250/305; 250/306; 250/311; 324/770
(58) Field of Search ........ 250/305–311, 440.11–449.11, 250/492.1, 492.2, 492.21, 498.22, 492.3, 491.3, 491.1, 397, 391, 441.1, 442.1, 445.1, 398, 497.2; 324/501, 770, 751, 771

(56) References Cited

U.S. PATENT DOCUMENTS

| | | | | |
|---|---|---|---|---|
| 3,629,579 A | * | 12/1971 | Naitou ........................ | 250/310 |
| 3,919,558 A | * | 11/1975 | Brouillette et al. ....... | 250/443.1 |
| 4,712,057 A | * | 12/1987 | Pau ............................ | 250/310 |
| 4,749,868 A | * | 6/1988 | Hatanaka et al. ......... | 250/443.1 |
| 4,814,615 A | * | 3/1989 | Fushimi et al. ............ | 250/311 |
| 5,057,689 A | * | 10/1991 | Nomura et al. ............ | 250/310 |
| 5,153,434 A | * | 10/1992 | Yajima et al. ............. | 250/311 |
| 5,204,617 A | * | 4/1993 | Kumagai .................... | 324/770 |
| 5,235,272 A | * | 8/1993 | Henley ....................... | 324/770 |
| 5,378,982 A | * | 1/1995 | Feigenbaum et al. ...... | 324/770 |
| 5,432,461 A | * | 7/1995 | Henley ....................... | 324/770 |
| 5,440,122 A | * | 8/1995 | Yasutake ................... | 250/443.1 |
| 5,459,409 A | * | 10/1995 | Henley ...................... | 324/770 |
| 5,506,516 A | * | 4/1996 | Yamashita et al. ......... | 324/770 |
| 5,539,326 A | * | 7/1996 | Takahashi et al. ......... | 324/770 |
| 5,546,013 A | * | 8/1996 | Ichioka et al. ............ | 324/770 |
| 5,576,833 A | * | 11/1996 | Miyoshi et al. ............ | 356/394 |
| 5,594,296 A | * | 1/1997 | Mitsutake et al. ......... | 313/309 |
| 5,694,053 A | * | 12/1997 | Smith ......................... | 324/770 |
| 5,793,221 A | * | 8/1998 | Aoki .......................... | 324/770 |
| 5,801,545 A | * | 9/1998 | Takekoshi et al. ......... | 324/770 |
| 5,982,190 A | * | 11/1999 | Toro-Lira .................. | 324/770 |
| 6,033,281 A | | 3/2000 | Toro-Lira | |
| 6,075,245 A | | 6/2000 | Toro-Lira | |
| 6,265,812 B1 | * | 7/2001 | Watanabe et al. ..... | 313/103 CM |
| 6,545,500 B1 | * | 4/2003 | Field .......................... | 324/770 |
| 6,587,581 B1 | * | 7/2003 | Matsuyama et al. ........ | 382/149 |
| 6,636,064 B1 | * | 10/2003 | Satya et al. ................ | 324/763 |

* cited by examiner

*Primary Examiner*—John R. Lee
*Assistant Examiner*—David A. Vanore
(74) *Attorney, Agent, or Firm*—Rankin, Hill, Porter & Clark LLP (57) ABSTRACT

A substrate holding pallet assembly of the present invention comprises a pallet for holding a substrate on upper face thereof, and a probe laid on said pallet from above so as to hold said substrate between said pallet and said probe. Also, a substrate inspection device of the invention comprises a chamber having an exhauster for exhausting the chamber into a high vacuum state, an electron beam generator for radiating an electron beam to the substrate, and a secondary electron detector for detecting a secondary electron generated from the substrate by radiation of electron beam from the electron beam generator, a pallet for holding the substrate on upper face thereof, and a probe laid on said pallet from above so as to hold said substrate between said pallet and said probe.

16 Claims, 7 Drawing Sheets

PALLET ASSEMBLY FOR SUBSTRATE INSPECTION DEVICE AND SUBSTRATE INSPECTION DEVICE

BACKGROUND OF THE INVENTION

1. Field of the Invention

The present invention relates to a pallet assembly for substrate inspection device and a substrate inspection device.

2. Description of the Related Art

One of the display devices using a liquid crystal substrate is a flat panel display (hereinafter referred to as an FPD) This FPD is a display device for displaying electronic information. One of the recent typical FPDs is a liquid crystal display (hereinafter an LCD) composed of a thin film transistor (hereinafter a TFT). The LCD composed of the TFT is employed for a high performance laptop computer.

The constitution and the operation of the LCD composed of the TFT will be described below. The LCD composed of the TFT has a fundamental structure of a liquid crystal panel in which a liquid crystal is poured between one glass substrate on which the TFT and pixel electrodes are formed and the other glass substrate on which counter electrodes are formed. In this specification, the one glass substrate on which the TFT and pixel electrodes are formed is defined as a substrate.

Figure 6:
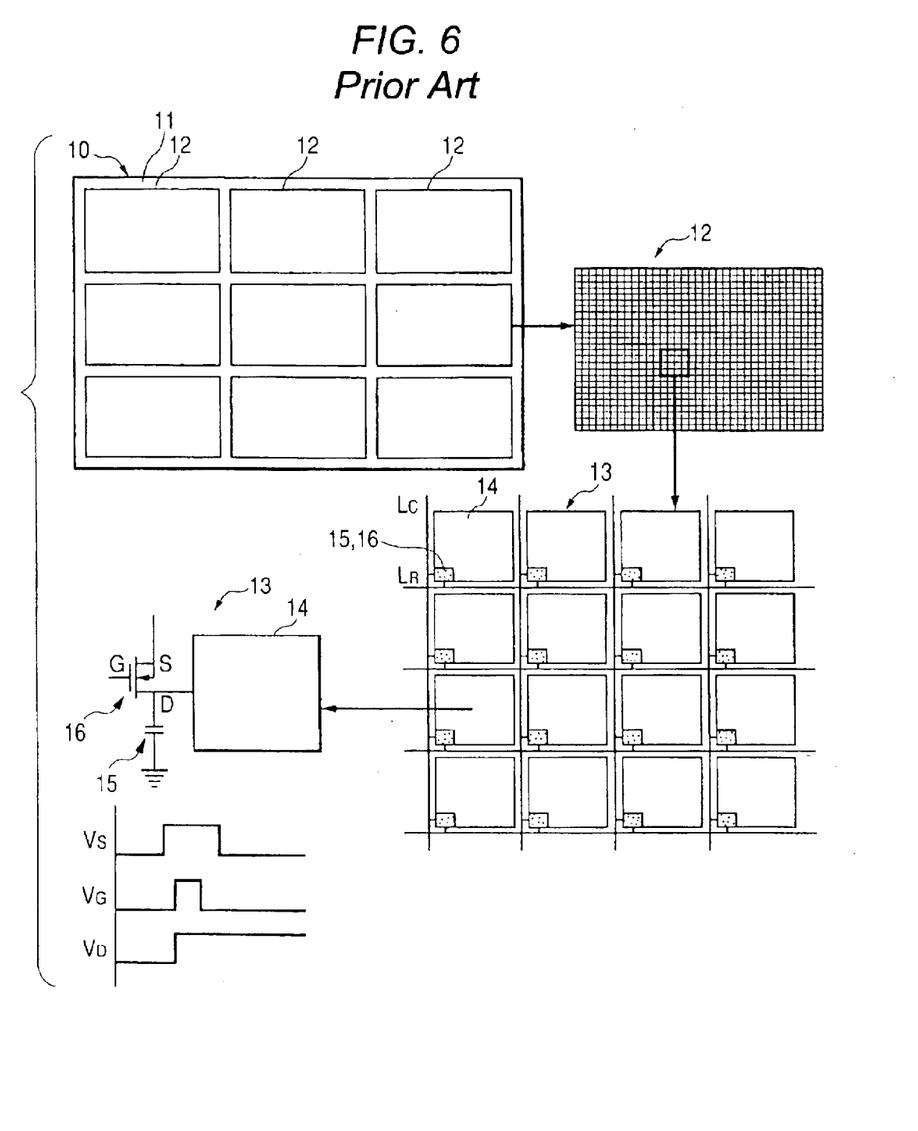
FIG. 6 is a schematic view showing a glass substrate on which the TFT and pixel electrodes are formed.

FIG. 6 is a schematic view of a substrate on which the TFT and pixel electrodes are formed. In FIG. 6, the substrate 10 has a plurality of panels formed on a single glass substrate 11 through a process for manufacturing a typical integrated circuit, each panel 12 being composed of a plurality of pixels 13 arrayed like a matrix.

Each pixel 13 comprises a pixel electrode 14, a storage capacitor 15 and the TFT 16. The pixel electrode 14 is formed from a light transmitting material, typically, ITO (Indium Tin Oxide). An electrode having a reference voltage of the pixel 13 applied within the storage capacitor 15 is grounded. Namely, the reference voltage of each TFT 16 is set to a ground level. The TFT 16 functions as a switch. A row selection signal $L_R$ for switching control is supplied to a gate electrode G of the TFT 16, and a column selection signal $L_C$ as the data signal is supplied to a source electrode S of the TFT 16.

In driving the pixels 13, when a voltage $V_S$ is applied to the source electrode S of the TFT 16 (i.e., when the column selection signal $L_C$ is supplied), if a voltage $V_G$ is applied to the gate electrode G (i.e., when the row selection signal $L_R$ is supplied), the TFT 16 is turned on to increase the drain voltage $V_D$. At this time, the storage capacitor 15 is charged to maintain a drain voltage $V_D$ till the next refresh cycle. By repeating this process for each pixel 13, a liquid crystal molecular array between two glass substrates is controlled to display a two-dimensional image on a liquid crystal display.

In the inspection of the substrate on which the TFT and pixel electrodes are formed, a method for determining a state of each pixel on the substrate without contact, employing the voltage contrast technique of electron beam was proposed U.S. Pat. No. 5,982,190). This substrate inspection method using the voltage contrast technique has the advantages that it is cheaper in the cost than the inspection method using the conventional mechanical probe, and faster in the inspection speed than the optical inspection method.

Figure 7:
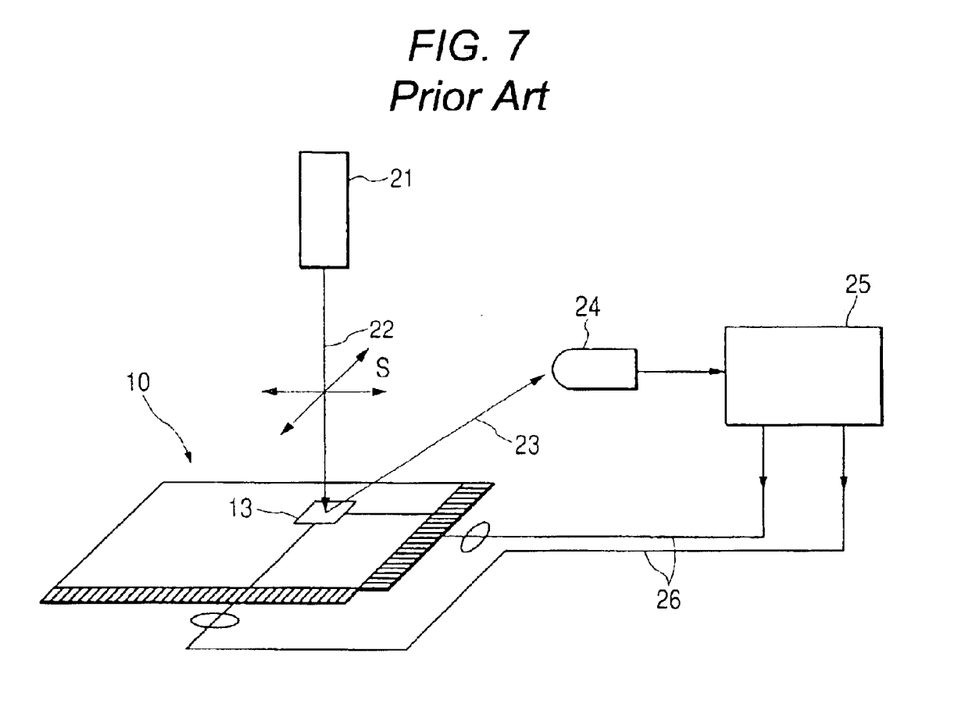
FIG. 7 is a view for explaining a method for inspecting the substrate employing the voltage contrast technique.

FIG. 7 is a view for explaining the substrate inspection method using the voltage contrast technique. This inspection method is made within a high vacuum chamber. The substrate to be inspected is conveyed to the high vacuum chamber, and inspected in a state where it is laid on the stage.

In FIG. 7, the inspection device comprises an electron beam generating source 21, a secondary electron detector 24 and a signal analyzer 25. The electron beam generating source 21 radiates an electron beam 22 to each pixel 13 of the substrate 10. The secondary electron detector 24 detects a secondary electron 23 generated by radiating the electron beam 22 to each pixel 13 of the substrate 10. Also, the secondary electron detector 24 outputs a signal representing a voltage waveform of pixel 13 to the signal analyzer 25 on the basis of the detected quantity of secondary electron 23. The signal analyzer 25 analyzes an output signal from the secondary electron detector 24 to inspect the state of pixel 13, particularly, the presence or absence or the content of defective pixel. Also, the signal analyzer 25 outputs a drive signal for electrically scanning each pixel 13 on the substrate 10 via a line 26. This scanning is performed in synchronism with the scanning on the substrate 10 as indicated by the arrow S with the electron beam 22.

A principle of the voltage contrast technique based on the detected quantity of secondary electron will be described below.

The quantity of secondary electron 23 discharged from each pixel 13 of the substrate 10 depends on an electrode for the voltage of pixel 13 on the substrate 10. For example, when the pixel 13 of the substrate 10 is driven positively, the secondary electron 23 generated by radiating the electron beam 22 to the pixel 13 has a negative electric charge, and is led into the pixel 13. As a result, the quantity of secondary electron 23 arriving at the secondary electron detector 24 is decreased.

On one hand, when the pixel 13 of the substrate 10 is driven negatively, the secondary electron 23 generated by radiating the electron beam 22 to the pixel 13 has a negative electric charge, and is repelled against the pixel 13. As a result, the quantity of secondary electron 23 generated from the pixel 13 arrives at the secondary electron detector 24.

In this manner, because the detected quantity of secondary electron 23 generated from the pixel 13 is affected by the polarity of voltage of the pixel 13, a voltage signal waveform of the pixel 13 is measured and the presence or absence of defective pixel is determined.

As above described, the inspection of the substrate is made within the high vacuum environment, and usually within a sealed chamber. Conventionally, this substrate was inspected in the state where it was laid directly on the stage within the chamber. In inspecting the substrate in this situation, the substrate might be broken within the sealed chamber, or a part of the apparatus comprising the chamber might be damaged. Namely, a glass substrate of the substrate might be fractured during the inspection, its fractions being scattered within the chamber to apart of the apparatus comprising the chamber, for example, a turbo molecular pump rotor for vacuum evacuation, damaging the apparatus. Also, it took a lot of trouble to draw back glass fractions scattered within the chamber and over the stage. Thus, it was apprehended conventionally that the apparatus might be damaged due to scattered fractions into the chamber or the withdrawal of fractions was made.

SUMMARY OF THE INVENTION

The present invention has been achieved in the light of the above affairs, and it is an object of the invention to provide a pallet assembly for substrate inspection device and a substrate inspection device for use with this pallet assembly, in which even when the substrate is broken with the inspection device, broken fractions can be easily withdrawn without damaging the inspection device.

In order to achieve the above object, this invention provides a substrate holding pallet assembly comprising a pallet for holding a substrate on upper face thereof, and a probe laid on said pallet from above so as to hold said substrate between said pallet and said probe.

It is preferable that concave grooves that receive conveyance unit for conveying the substrate are formed on the upper face of the pallet. In addition to this, one concave groove may be employed on the pallet.

Also, it is preferable that the pallet comprises a position alignment mechanism for aligning the position of the substrate on the pallet when the substrate is laid.

Also, it is preferable that the pallet comprises an electrode in contact with an external power supply, a feeding portion for applying a voltage from the electrode to a prober, and a flexible circuit for connecting the electrode with the feeding portion, and the prober comprises an electrode in contact with a feeding portion of the pallet, and probe pins for applying a voltage from the electrode to the substrate, the probe pins being mounted via an insulating member to the prober.

Also, in order to solve the above object, this invention provides a substrate inspection device comprising a chamber having an exhauster for exhausting the chamber into a high vacuum state, an electron beam generator for radiating an electron beam to the substrate, and a secondary electron detector for detecting a secondary electron generated from the substrate by radiation of electron beam from the electron beam generator, a pallet for holding the substrate on upper face thereof, and a probe laid on said pallet from above so as to hold said substrate between said pallet and said probe.

It is preferable that concave grooves that receive conveyance unit for conveying the substrate are formed on the upper face of the pallet.

Also, it is preferable that the pallet comprises a position alignment mechanism for aligning the position of the substrate on the pallet when the substrate is laid.

Also, it is preferable that the pallet comprises an electrode in contact with an external power supply, a feeding portion for applying a voltage from the electrode to a prober, and a flexible circuit for connecting the electrode with the feeding portion, and the prober comprises an electrode in contact with a feeding portion of the pallet, and probe pins for applying a voltage from the electrode to the substrate, the probe pins being mounted via an insulating member to the prober.

Also, it is preferable that the chamber is composed of a preliminary chamber having the exhauster and connected via an openable and closable first partition wall to the outside, and a main chamber having the electron beam generator and a secondary electron generator, and wherein the preliminary chamber and the main chamber are connected via an openable and closable second partition wall, and further comprising conveyance unit for conveying the pallet assembly between the preliminary chamber and the main chamber.

Also, it is preferable that at least two the preliminary chambers are provided for each one main chamber.

In the inspection device of the above constitution, even if the substrate is broken within the chamber, the fractions remain within the pallet assembly, and do not splash into the chamber. Accordingly, even if the glass substrate of the substrate is broken during the inspection, glass fractions do not splash into the chamber to damage a part of the device constituting the chamber.

Also, even if the glass substrate is broken within the chamber, the fractions do not splash into the chamber but remain within the pallet assembly, and thereby can be easily collected by withdrawing the pallet assembly.

DETAILED DESCRIPTION OF THE PREFERRED EMBODIMENTS

The preferred embodiments of the present invention will be described below in detail with reference to the accompanying drawings.

Figure 1A:
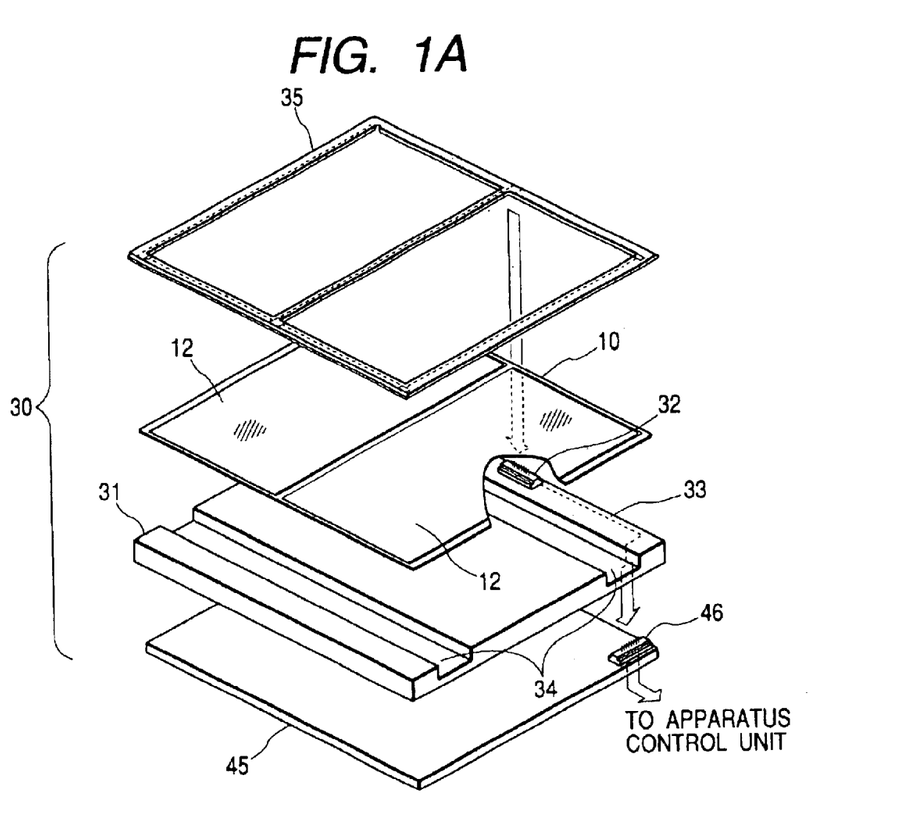
FIGS. 1A and 1B are perspective views showing how to fix a substrate between a substrate holding pallet assembly according to a first embodiment of the present invention and a source voltage applying prober.
Figure 1B:
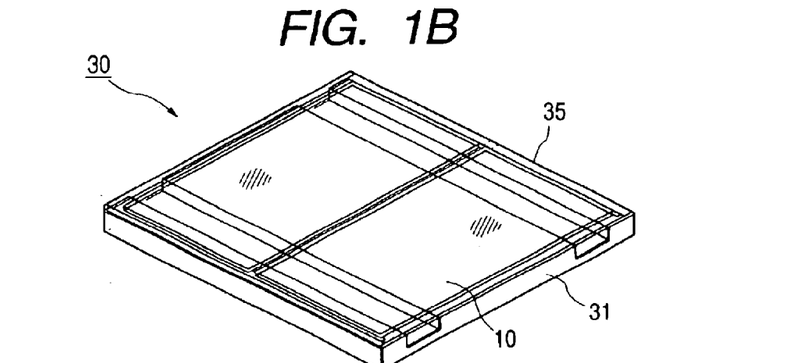

FIGS. 1A and 1B are views showing a pallet assembly for use with a substrate inspection device according to a first embodiment of the invention. This substrate inspection device has the same constitution as the conventional inspection device as previously described, in which the parts having the same operation are designated by the same reference numerals, and description of those parts is omitted.

FIG. 1A is a perspective view showing a form for fixing a substrate between a substrate holding pallet assembly and a source voltage applying probe. Herein, a substrate 10 has two panels 12 formed on a glass substrate, as shown in FIG. 1A.

As shown in FIG. 1A, a pallet assembly for substrate inspection device 30 of the first embodiment is roughly composed of a pallet 31 and a source voltage applying prober (hereinafter a prober) 35. The pallet 31 has an electrode (not shown) formed thereon so as to be opposed to a feeding portion 46 of a stage 45 of the substrate inspection device and contacted with the feeding portion 46 on the stage 45 opposed thereto, a feeding portion 32 provided on the side of the pallet 31 and in contact with an electrode (not shown) of the prober 35, and a flexible circuit 33 for connecting the feeding portion 32 with the electrode in contact with the feeding portion 46. The pallet 31 holds the substrate 10 on its upper face.

The prober 35 has a shape of covering a glass portion except for an area where the panels 12 are formed on the substrate 10. For example, in FIG. 1A, the prober 35 has a frame shape surrounding two panels 12 formed on the glass substrate. Also, the prober 35 has an electrode (not shown) in contact with the feeding portion 32 for the pallet 31, and a probe pin (not shown) in contact with the electrode connected to the panel 12 and provided on the opposed glass substrate. The probe pin is connected via the wiring to an electrode (in contact with the feeding portion 32) and formed on the prober 35 so as to be opposed to the pallet 31 to apply a voltage from the electrode to the electrode on the glass substrate. Herein, the probe pins are attached via an insulating member made of ceramics to the prober 35. With the above constitution, the prober 35 supplies a drive signal to each pixel on the substrate 10, and is employed for the inspection method as above described.

The pallet 31 carries the substrate 10 between the prober 35 and it in a state where the substrate 10 is laid thereon, and the prober 35 is disposed on the substrate 10. The probe pin (not shown) of the prober 35 supplies a drive signal to each pixel on the substrate 10.

The pallet 31 and the prober 35 are fastened together by a fixing member such as a bolt (FIG. 1B).

The pallet assembly for substrate inspection device formed in the above manner is laid on the stage 45 for an inspection device. At this time, the feeding portion 46 provided on the stage 45 and the electrode of the pallet 31 are connected. In the inspection device, the pallet 31 (and the prober 35) is grounded and electrically insulated. Herein, the pallet 31 may be as large as 680 mm×880 mm, for example. The material of the pallet 31 and the prober 35 may be aluminum 5052, for example.

However, the material of the pallet 31 may be arbitrary as far as the upper face of the pallet 31 has a secure smoothness and is not charged. If the pallet 31 is charged, the pallet 31 is discharged in taking out the substrate 10, bringing about a danger of breaking down the TFT.

Figure 2:
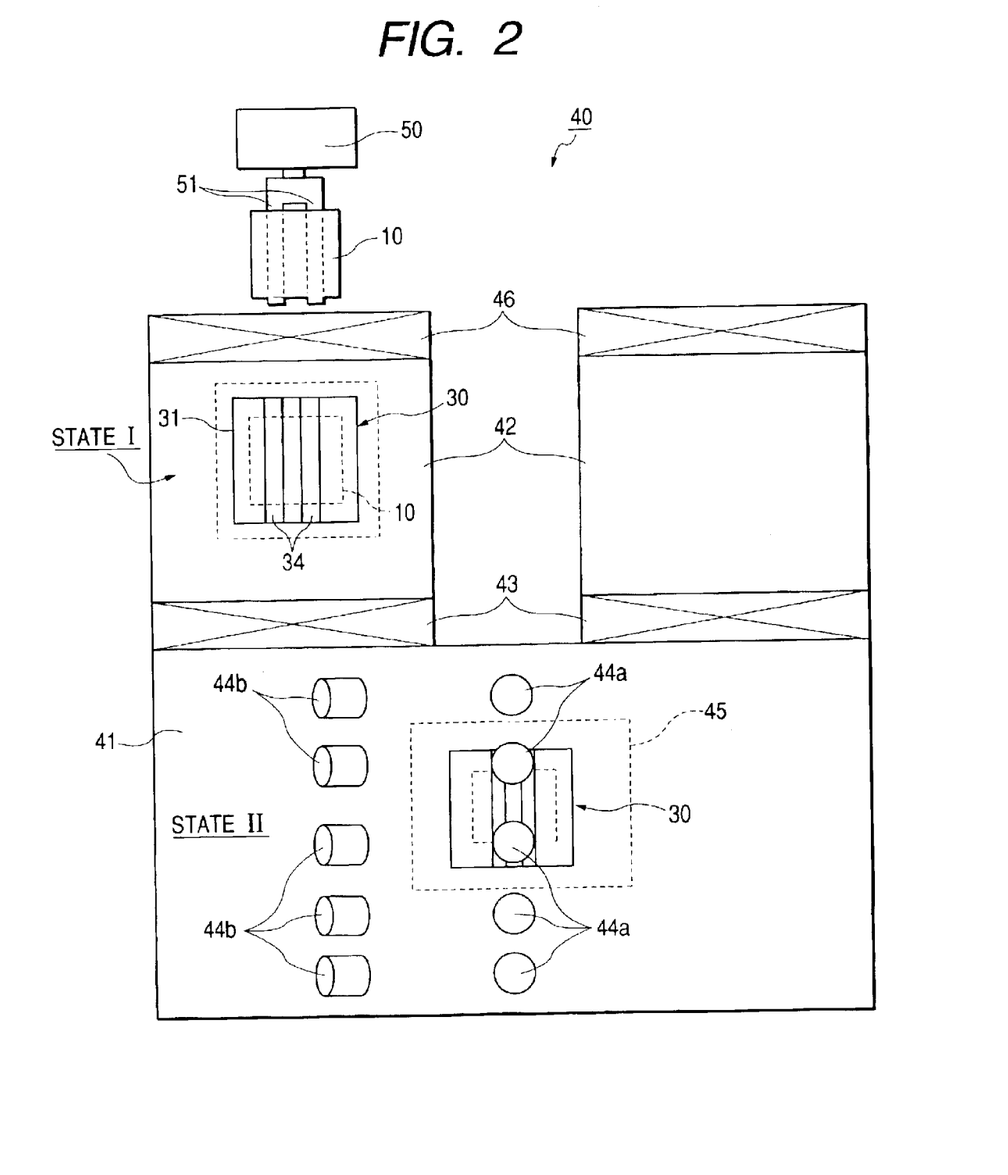
FIG. 2 is a view schematically showing a substrate inspection device according to the first embodiment of the invention.

The substrate inspection device 40 employing this substrate inspection pallet assembly 30 will be described below. FIG. 2 is a schematic constitution view of this substrate inspection device 40.

The substrate inspection device 40 as shown in FIG. 2 is composed of a main chamber 41 for making the electronic beam inspection, and a preliminary chamber 42 connected to the main chamber 41 and communicating to the outside of the device. The main chamber 41 comprises the electron guns 44a for radiating a secondary electron detector 44b for detecting a secondary electron, and is internally kept in a high vacuum state. The preliminary chamber 42 has a first partition wall (hereinafter a door valve) 46 that is openable or closable, and communicates chamber 42 has an exhauster such as a molecular turbo pump that compulsorily exhausts the preliminary chamber 42 of the air. A second partition wall (hereinafter a gate valve) 43 is provided between the main chamber 41 and the preliminary chamber 42, whereby the main chamber 41 and the preliminary chamber 42 can be independently placed in a vacuum state. Also, the preliminary chamber 42 comprises a conveyance robot, not shown. The pallet assembly laid within the preliminary chamber is conveyed to the stage 45 provided within the main chamber by this conveyance robot. The stage 45 within the main chamber 41 is moved in the main chamber 41 to convey the pallet assembly to an optimal position for inspection.

In inspecting the substrate employing the inspection device 40, first of all, the substrate 10 as an objective for inspection conveyed by a loader robot 50 (conveying unit) is laid on the pallet 31 of the pallet assembly 30. A hand portion 51 of the loader robot 50 is received in a concave groove 34 (see FIG. 1A) provided on an upper face of the pallet 31 to lay the substrate 10 thereon securely, in which the hand portion 51 alone can be pulled out quickly. In this structure, the prober 35 and the pallet 31 are fastened via fastener unit, not shown, such as a bolt in advance(see FIG. 1B) (state I).

When the substrate as an objective for inspection is inspected in the substrate inspection device 40, first of all, the door valve 46 is closed to shut off the preliminary chamber 42 from the outside, whereby the preliminary chamber 42 is compulsorily exhausted of the air by the exhauster, not shown. If the preliminary chamber 42 is exhausted in the same high vacuum state as the main chamber 41, the gate valves 43 for the preliminary chamber 42 and the main chamber 41 are opened, and communicated. Then, the conveyance robot within the preliminary chamber 42 conveys the pallet assembly 30 having the substrate to the stage 45 within the main chamber 41. The substrate 10 and the pallet assembly 30 conveyed into the main chamber 41 are moved to the inspection position along with the movement of the stage 45, and inspected by the electron guns. 44a and the secondary electron detecting unit 44b within the main chamber 41 (state II).

In making the inspection, the substrate 10 is placed on the stage 45 in a state where it is fixed between the pallet assembly 31 and the prober 35, and conveyed to the high vacuum chamber. In an inspection process, a source voltage is supplied from a device control unit, not shown, via the feeding portion 46 of the stage 45, and the flexible circuit 33 and the feeding portion 32 of the pallet 31 to the electrode of the prober 35. And a drive signal is supplied from the probe pin of the prober 35 via the electrode on the substrate 10 to each pixel 13 of the substrate 10.

The inspected substrate is conveyed into the preliminary chamber 42 by the movement of the stage 45 and the conveyance of the conveyance robot again. After the pallet assembly 30 is moved into the preliminary chamber 42, the gate valve 43 between the main chamber 41 and the preliminary chamber 42 is closed, so that the inside of the preliminary chamber 42 is pressurized in a state equivalent to the outside by pressurizing unit, not shown. If the inside of the preliminary chamber 42 reaches the same pressure as the atmospheric pressure of the outside, the door valve 46 is opened and the inspected substrate 10 is taken out of the pallet assembly 30.

In the inspection device 40 of the above constitution, even if the glass substrate for the substrate 10 is broken within the chamber, glass fractions remain within the pallet assembly 30, and do not splash to the stage within the chamber or other devices. Therefore, it is possible to suppress the damage of the device due to splashed fractions to the minimum. Also, the fractions can be easily collected by withdrawing the pallet assembly. Furthermore because a glass portion on the substrate 10 is covered with the prober 35, it is possible to supply a drive signal to each pixel 13, while preventing the glass portion from being charged negatively (overcharged) by the electron beam 22. The inspection device 40 as shown in the figure has two preliminary chambers 42 of the same constitution. For these two preliminary chambers 42, while one preliminary chamber is performing the depressurized/pressurized operation, the pallet assembly within the other preliminary chamber depressurized beforehand can be conveyed to the main chamber and inspected. In this way, the main chamber can be also used for inspection for a period while the preliminary chamber is depressurized or pressurized, whereby the inspection can be efficiently made.

FIGS. 3 to 5C are views showing a pallet 60 for use with the substrate inspection device 40 according to a second embodiment of the invention. The same or like parts in constitution and operation are designated by the same reference numerals as in the conventional inspection device 40.

Figure 3:
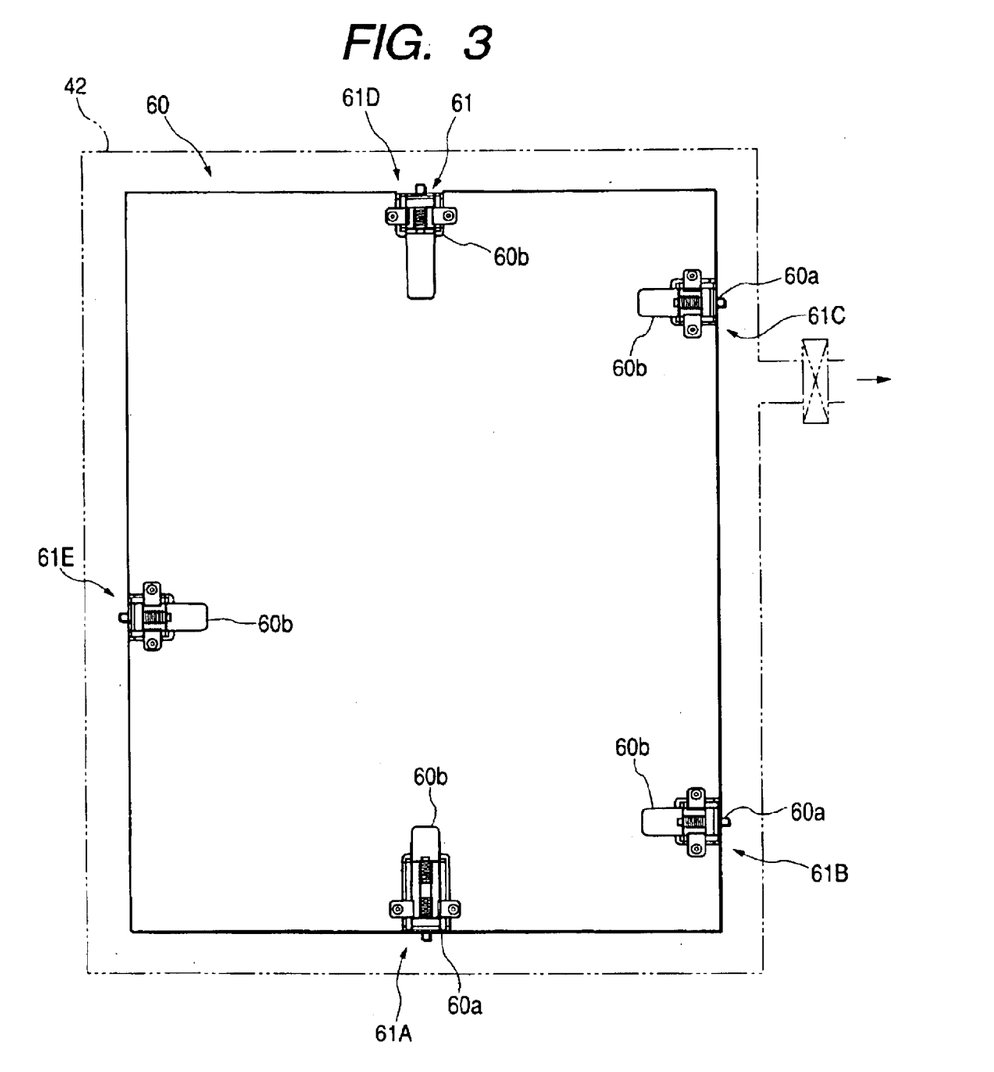
FIG. 3 is a view schematically showing a substrate holding pallet assembly having a position alignment mechanism according to a second embodiment of the invention.

Referring to FIG. 3, the pallet 60 for the substrate inspection device 40 according to the second embodiment of the invention comprises the pallet having five alignment units 61A to 61E mounted. Each alignment unit is mounted at least one on each side of the almost rectangular pallet 60. The prober, not shown, is the same as in the first embodiment of the invention. At this time, each of the alignment units 61A, 61B and 61C is provided with a reference wall 60a for determining a desired substrate alignment position, whereby the substrate is moved till a part of the alignment unit abuts against the reference 15 wall 60a. On one hand, each of the alignment units 61D and 61E continues to push the substrate up to the substrate alignment position where the movement of the alignment units 61A, 61B and 61C is finally completed. Herein, the substrate alignment position unit the set position on the pallet at which the substrate is laid, because it is necessary to lay the substrate at a predetermined position on the pallet to apply correctly electron beam to a predetermined region of the substrate in the inspection process.

Figure 4A:
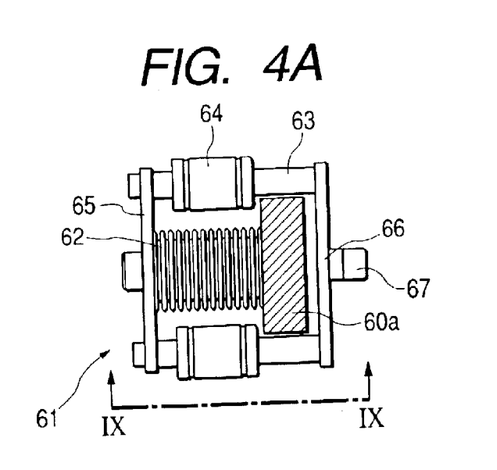
FIGS. 4A to 4C are views showing a position alignment device constituting the position alignment mechanism as shown in FIG. 3.
Figure 4B:
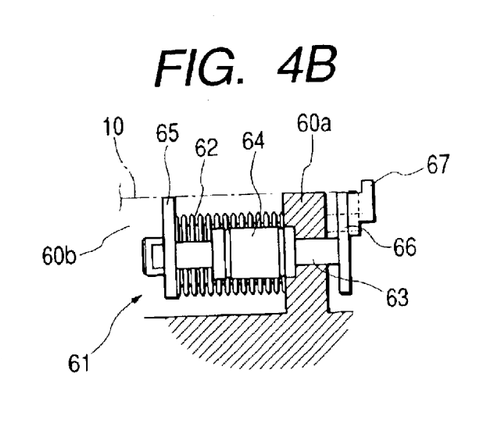
Figure 4C:
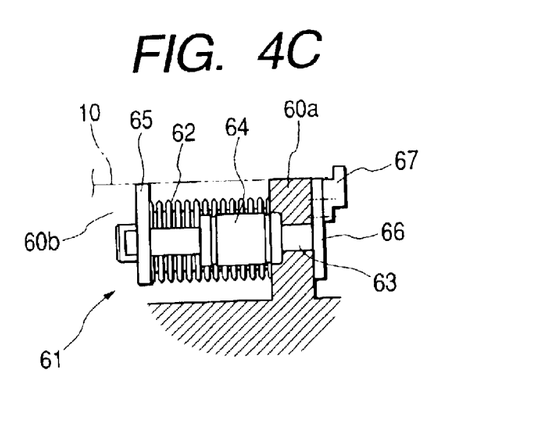

FIGS. 4A to 4C are detailed views showing the alignment units 61A to 61C. FIG. 4A is a view of an alignment unit 61, as looked from the above. This alignment unit 61 comprises a vacuum bellows 62, a pair of cylindrical members 64 disposed in parallel to this vacuum bellows 62 and fixed to the pallet 60, a pair of sliding shafts 63 attached slidably to the cylindrical members 64, an inner connection member 65 and an outer connection member 66 for connecting these sliding shafts 63, and a projection 67 provided on the outer connection member 65 for moving the substrate. The reference wall 60a may be provided integrally or separately on the pallet 60. The vacuum bellows has a vacuum inside, and is contracted in the atmosphere, in which if the preliminary chamber 42 is exhausted of the air, the bellows extends due to a resilient force of the bellows itself caused by a reduced pressure difference.

This alignment unit 61 is provided on an upper face of the pallet 60 where the substrate is laid, and received within a alignment unit receiving concave portion 60b that is configured to receive the whole oft he alignment unit 61. Also, even though the alignment unit is received within the receiving concave portion 60b, none is protruded from the upper face of the pallet 60 where the substrate 10 is laid, except for the projection 67 for moving the substrate. The vacuum bellows 62 of the alignment unit 61 received within the receiving concave portion 60b has one end attached to an inner end face, and the other end attached to the inner connection member 65 located within the receiving concave portion 60b. Furthermore, this inner connection member 65 is connected to one end of the pair of sliding shafts 63. Also, the other end of the pair of sliding shafts 63 is connected to the outer connection member 66. Accordingly, the inner connection member 65 and the outer connection member 66 are moved relative to the cylindrical members 64 secured to the pallet 60 along with the sliding of the shafts 63 (see FIGS. 4B and 4C). Moreover, the outer connection member 66, the projection 67 and a part of the sliding shaft 63 of this alignment unit 61 are disposed outside the desired substrate alignment position formed on the upper face of the pallet 60 in the atmospheric pressure.

Referring to FIGS. 4A to 4C, the operation of this alignment unit 61 will be described below. FIGS. 4B and 4C are views as seen from the arrow IX. In the alignment unit 61 as shown in FIG. 4A, the inner connection member 65 is moved so as to be pulled from the inner end face (left end face in the figure) of the reference wall 60a by the vacuum bellows 62 contracted under the atmospheric pressure environment. Since this inner connection member 65 is moved by shrinking of the vacuum bellows 62, the outer connection member 66 is moved toward the outer end face (right end face in the figure) of the reference wall 60a via the sliding shafts 63. That is, the projection 67 formed on the outer connection member 66 projects greatly from the outer end face of the reference wall 60a under the atmospheric pressure environment. In this manner, the projection 67 is disposed outside the desired substrate alignment position formed on the upper face of the pallet 60 at the atmospheric pressure.

FIG. 4C is a view showing an instance where the pallet 60 having the alignment unit 61 is received within the vacuum chamber and the vacuum chamber is evacuated. Under the vacuum environment, the vacuum bellows 62 extends due to a resilient force of the bellows itself. Accordingly, the inner connection member 65 is moved inwards from the inner end face of the reference wall 60a due to a resilient force of the vacuum bellows. Along with the movement of this inner connection member 65, the outer connection member 66 is pulled by the sliding shaft 63 till making contact with the outer end face of the reference wall 60a. Namely, the projection 67 formed on the outer connection member 66 is moved in an inner circumferential direction of the pallet 60, till the outer connection member 66 makes contact with the outer end face of the reference wall 60a. In this manner, the movement of the outer connection member 66 is restricted, and the movement of the projection 67 is also restricted. The alignment units 61D and 61E have the same constitution as the alignment units 61A to 61C, except that the reference wall 60a is not provided.

Figure 5A:
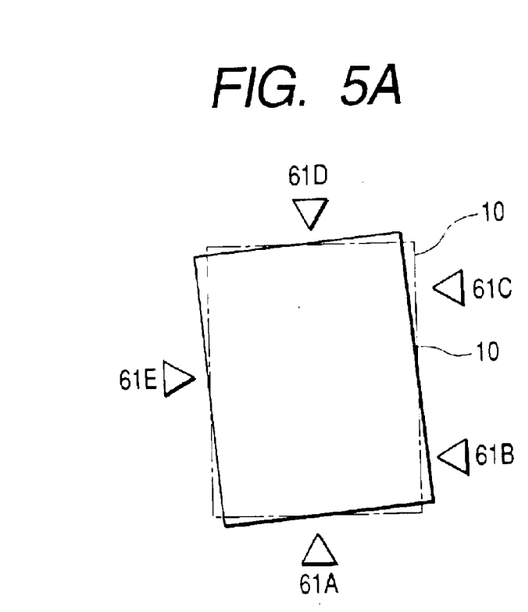
FIGS. 5A to 5C are views for explaining the operation of the position alignment mechanism as shown in FIGS. 3 and 4A to 4C.
Figure 5B:
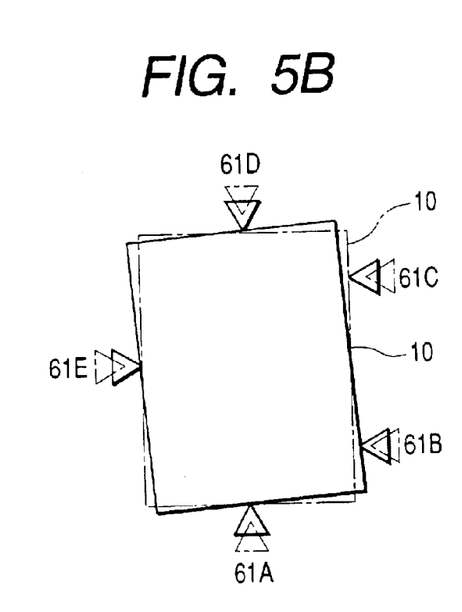
Figure 5C:
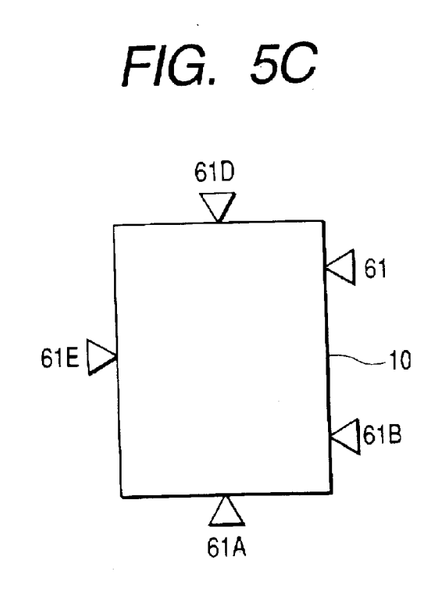

Referring to FIGS. 5A to 5C, an operation of adjusting the position of the substrate 10 laid on the pallet 60 by exhausting the chamber and activating the alignment unit as shown in FIGS. 4B and 4C will be described below.

FIG. 5A typically shows the substrate 10 laid on the pallet 60 with the alignment units 61A to 61E. In FIG. 5A, the substrate laid on the pallet is indicated by the solid line, and the desired region for disposing the substrate is indicated by the broken line. Also, the projection 67 of the alignment unit is indicated by the triangle. The state of FIG. 5A is an initial state where the substrate is laid on the pallet, in which the vacuum bellows of the alignment unit is contracted under the outer air environment.

The vacuum bellows 62 starts to extend by exhausting the air from the vacuum chamber gradually because a pressure difference within the vacuum bellows 62 is resolved, as shown in FIG. 5B. Then, the projection 67 (triangle in the figure) of the alignment mechanism is moved in the inner circumferential direction of the pallet, along with the extension of the vacuum bellows 62. Accordingly, the substrate 10 is gradually moved to a predetermined alignment position, while being pushed by five alignment units 61A to 61E disposed on the pallet. In the figure, the projection of the alignment unit 61 is moved from the position of the solid line to the position of the broken line.

FIG. 5C shows a state where the chamber is evacuated. Since the vacuum chamber is placed in a vacuum state, the extension of the vacuum bellows is completed, and the projection of the alignment unit gets to a position where a desired substrate position is attained. In this manner, the substrate laid on the pallet is located at desired position. The projections of the alignment units 61A, 61B and 61C move the substrate 10 till the outer member 66 abuts against the reference wall 60a. Also, the alignments 61D and 61E without the reference wall 60a continue to push the substrate 10, and finally arrive at an alignment completed position where the movement of the alignments 61A, 61B and 61C is completed.

With the second embodiment of the invention, the vacuum bellows allows the alignment of the substrate to be made utilizing the evacuation of the chamber, without employing the motor. Thereby, special regard is not taken about a discharge gas from the drive unit disposed as the alignment unit. Also, there is no need of leading a cable due to the use of an electric motor member such as a motor for the alignment unit, whereby the design of the alignment mechanism is simplified.

The present invention is not limited to the above embodiments, but may be employed in combination of the embodiments. Also, the prober and the pallet may be connected via a crank. Moreover, the fastener unit for fastening the prober and the substrate holding unit is not limited to the bolt, but may be a clip.

what is claimed is:

1. A substrate inspection device comprising:
   a chamber having:
      an exhauster for exhausting said chamber into a high vacuum state;
      an electron beam generator for radiating an electron beam to said substrate; and
      a secondary electron detector for detecting a secondary electron generated from said substrate by radiation of electron beam from said electron beam generator;
   a pallet for holding said substrate on an upper face thereof; and
   a prober laid on said pallet from above so as to hold said substrate between said pallet and said prober.

2. The substrate inspection device according to claim 1, further comprising a position alignment mechanism for aligning a position of said substrate on said pallet when said substrate is laid upon said pallet upper face.

3. The substrate inspection device according to claim 1, wherein said pallet comprises an electrode in contact with an external power supply, a feeding portion for applying a voltage from said electrode to said prober, and a flexible circuit for connecting said electrode with said feeding portion, and
   said prober comprises an electrode in contact with a feeding portion of said pallet, and probe pins for applying a voltage from said electrode to said substrate.

4. The substrate inspection device according to claim 1, wherein said chamber is composed of a preliminary chamber having said exhauster and connected via an openable and closable first partition wall to the outside, and a main chamber having said electron beam generator and said secondary electron detector, and
   wherein said preliminary chamber and said main chamber are connected via an openable and closable second partition wall, and further comprising a conveyance unit for conveying said pallet assembly between said preliminary chamber and said main chamber.

5. A substrate inspection device comprising:
   a chamber having:
      an exhauster for exhausting said chamber into a high vacuum state;
      an electron beam generator for radiating an electron beam to said substrate; and
      a secondary electron detector for detecting a secondary electron generated from said substrate by radiation of electron beam from said electron beam generator;
   a pallet for holding said substrate on an upper face thereof, an upper face of said pallet having concave grooves formed therein, said grooves being adapted to receive a conveyance unit for conveying said substrate; and
   a prober laid on said pallet from above so as to hold said substrate between said pallet and said prober.

6. The substrate inspection device according to claim 5, wherein at least two said preliminary chambers are provided for each one main chamber.

7. The substrate inspection device according to claim 5, further comprising a position alignment mechanism for aligning a position of said substrate on said pallet when said substrate is laid upon said pallet upper face.

8. The substrate inspection device according to claim 5, wherein said pallet comprises an electrode in contact with an external power supply, a feeding portion for applying a voltage from said electrode to said prober, and a conductor for electrically connecting said electrode with said feeding portion, and
   said prober comprises an electrode in contact with a feeding portion of said pallet, and probe pins for applying a voltage from said electrode to said substrate.

9. The substrate inspection device according to claim 8, wherein said conductor is a flexible circuit.

10. The substrate inspection device according to claim 5, wherein said chamber is composed of a preliminary chamber having said exhauster and connected via an openable and closable first partition wall to the outside, and a main chamber having said electron beam generator and said secondary electron detector, and
    wherein said preliminary chamber and said main chamber are connected via an openable and closable second partition wall, and further comprising a conveyance unit for conveying said pallet assembly between said preliminary chamber and said main chamber.

11. A substrate inspection device comprising:
    a chamber having:
       an exhauster for exhausting said chamber into a high vacuum state;
       an electron beam generator for radiating an electron beam to said substrate; and
       a secondary electron detector for detecting a secondary electron generated from said substrate by radiation of electron beam from said electron beam generator;
    a pallet for holding said substrate on an upper face thereof; and
    a prober laid on said pallet from above so as hold said substrate between said pallet and said prober, whereby said prober, substrate, and pallet are adapted to be moved together as a unit into and out of said chamber.

12. The substrate inspection device according to claim 11, further comprising a stage that receives said pallet and to which said pallet is electrically connected.

13. The substrate inspection device according to claim 12, wherein said prober is electrically connected to said pallet.

14. The substrate inspection device according to claim 11, further comprising a position alignment mechanism for aligning a position of said substrate on said pallet when said substrate is laid upon said pallet upper face.

15. The substrate inspection device according to claim 11, wherein said pallet comprises an electrode in contact with an external power supply, a feeding portion for applying a voltage from said electrode to said prober, and a flexible circuit for connecting said electrode with said feeding portion, and said prober comprises an electrode in contact with a feeding portion of said pallet, and probe pins for applying a voltage from said electrode to said substrate.

16. The substrate inspection device according to claim 11, wherein said chamber is composed of a preliminary chamber having said exhauster and connected via an openable and closable first partition wall to the outside, and a main chamber having said electron beam generator and said secondary electron detector, and wherein said preliminary chamber and said main chamber are connected via an openable and closable second partition wall, and further comprising a conveyance unit for conveying said pallet assembly between said preliminary chamber and said main chamber.

* * * * *